US008470804B2

(12) United States Patent
Berniac et al.

(10) Patent No.: US 8,470,804 B2
(45) Date of Patent: Jun. 25, 2013

(54) 11A, 12-DERIVATIVES OF TETRACYCLINE COMPOUNDS

(75) Inventors: Joel Berniac, Stoneham, MA (US); Mohamed Y. Ismail, Bedford, MA (US); Mark L. Nelson, Norfolk, MA (US); Faye Seyedi, Mansfield, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 13/340,040

(22) Filed: Dec. 29, 2011

(65) Prior Publication Data

US 2012/0101070 A1   Apr. 26, 2012

Related U.S. Application Data

(66) Continuation of application No. 11/348,608, filed on Feb. 6, 2006, now Pat. No. 8,088,755, Substitute for application No. 60/650,031, filed on Feb. 4, 2005.

(51) Int. Cl.
*A61K 31/65* (2006.01)
*C07C 237/26* (2006.01)

(52) U.S. Cl.
USPC .......................................... 514/152; 552/205

(58) Field of Classification Search
USPC .......................................... 552/205; 514/152
See application file for complete search history.

(56) References Cited

U.S. PATENT DOCUMENTS

| | | |
|---|---|---|
| 2,980,584 A | 4/1961 | Hammer |
| 2,990,331 A | 6/1961 | Neumann et al. |
| 3,007,965 A | 11/1961 | Growich, Jr. et al. |
| 3,062,717 A | 11/1962 | Hammer |
| 3,165,531 A | 1/1965 | Blackwood et al. |
| 3,183,267 A | 5/1965 | Balckwood et al. |
| 3,219,671 A | 11/1965 | Hlavka et al. |
| 3,226,436 A | 12/1965 | Petisi et al. |
| RE26,253 E | 8/1967 | Patisi et al. |
| 3,338,963 A | 8/1967 | Petisi et al. |
| RE26,271 E | 9/1967 | Boothe et al. |
| 3,341,585 A | 9/1967 | Bitha et al. |
| 3,345,379 A | 10/1967 | Martell et al. |
| 3,345,410 A | 10/1967 | Winterbottom et al. |
| 3,350,557 A | 10/1967 | Szymanski |
| 3,360,561 A | 12/1967 | Zambrano |
| 3,373,196 A | 3/1968 | Bitha et al. |
| 3,397,230 A | 8/1968 | Winterbottom et al. |
| 3,403,179 A | 9/1968 | Zambrano |
| 3,433,834 A | 3/1969 | Winterbottom et al. |
| 3,454,697 A | 7/1969 | Joyner et al. |
| 3,483,251 A | 12/1969 | Zambrano |
| 3,518,306 A | 6/1970 | Martell et al. |
| 3,557,280 A | 1/1971 | Weber et al. |
| 3,579,579 A | 5/1971 | Ross et al. |
| 3,609,188 A | 9/1971 | Esse et al. |
| 3,674,859 A | 7/1972 | Beutel et al. |
| 3,957,980 A | 5/1976 | Noseworthy |
| 4,018,889 A | 4/1977 | Armstrong |
| 4,024,272 A | 5/1977 | Rogalski et al. |
| 4,126,680 A | 11/1978 | Armstrong |
| 4,806,372 A | 2/1989 | Strumskis |
| 5,021,407 A | 6/1991 | Levy |
| 5,248,797 A | 9/1993 | Sum |
| 5,258,371 A | 11/1993 | Golub et al. |
| 5,281,628 A | 1/1994 | Hlavka et al. |
| 5,284,963 A | 2/1994 | Sum et al. |
| 5,326,759 A | 7/1994 | Hlavka et al. |
| 5,328,902 A | 7/1994 | Sum et al. |
| 5,371,076 A | 12/1994 | Lee et al. |
| 5,380,888 A | 1/1995 | Sum et al. |
| 5,386,041 A | 1/1995 | Sum et al. |
| 5,401,729 A | 3/1995 | Sum et al. |
| 5,401,863 A | 3/1995 | Hlavka et al. |
| 5,420,272 A | 5/1995 | Sum et al. |
| 5,430,162 A | 7/1995 | Sum et al. |
| 5,442,059 A | 8/1995 | Sum et al. |
| 5,457,096 A | 10/1995 | Sum et al. |
| 5,466,684 A | 11/1995 | Sum et al. |
| 5,494,903 A | 2/1996 | Hlavka et al. |
| 5,495,018 A | 2/1996 | Sum et al. |
| 5,495,030 A | 2/1996 | Sum et al. |
| 5,495,031 A | 2/1996 | Sum et al. |
| 5,512,553 A | 4/1996 | Sum et al. |
| 5,529,990 A | 6/1996 | Hlavka et al. |
| 5,530,117 A | 6/1996 | Hlavka et al. |
| 5,567,692 A | 10/1996 | Sum et al. |
| 5,567,693 A | 10/1996 | Backer et al. |
| 5,589,470 A | 12/1996 | Levy |
| 5,675,030 A | 10/1997 | Krishnan et al. |
| 5,811,412 A | 9/1998 | Levy |
| 5,843,925 A | 12/1998 | Backer et al. |

(Continued)

FOREIGN PATENT DOCUMENTS

| | | |
|---|---|---|
| DE | 1076679 B | 3/1960 |
| DE | 2346535 A1 | 4/1974 |

(Continued)

OTHER PUBLICATIONS

Barden, Timothy C. et al., "'Glycylcyclines'. 3. 9-Aminodoxycyclinecarboxamides," J. Med. Chem., vol. 37:3205-3211 (1994).
Bartzatt, Ronald et al., "Synthesis and Analysis of a Methyl Ether Derivative of Tetracydine Which Inhibits Growth of *Escherichia coli*," Physiol. Chem. Phys. & Med. NMR, vol. 34:71-81 (2002).
Bartzatt, Ronald et al., "Synthesis and analysis of ethylated tetracycline, an antibiotic derivative that inhibits the growth of tetracycline-resistant XL I-Blue bacteria," Biotechnol. Appl. Biochem., vol. 33:65-69 (2001).
Berens, Christian et al., "Subtype Selective Tetracycline Agonists and their Application for a Two-Stage Regulatory System," ChemBioChem., vol. 7:1320-1324 (2006).
Boothe, James H. et al., "6-Deoxytetracyclines. I. Chemical Modification by Electrophilic Substitution," J. Am. Chem. Soc., vol. 82:1253-1254 (1960).
International Search Report for Application No. PCT/US2006/004233, dated Jul. 13, 2006.
Koza, Darrell J. et al., "Palladium Catalyzed C-N Bond Formation in the Synthesis of 7-Amino-Substituted Tetracyclines," J. Org. Chem., vol. 67:5025-5027 (2002).

(Continued)

*Primary Examiner* — Barbara P Badio
(74) *Attorney, Agent, or Firm* — McCarter & English, LLP; Elizabeth A. Hanley

(57) ABSTRACT

11a,12-dehydrotetracycline compounds are described.

13 Claims, No Drawings

U.S. PATENT DOCUMENTS

| | | | |
|---|---|---|---|
| 5,856,315 | A | 1/1999 | Backer et al. |
| 5,886,175 | A | 3/1999 | Sum et al. |
| 6,256,365 | B1 | 7/2001 | Lai |
| 6,500,812 | B2 | 12/2002 | Nelson et al. |
| 6,506,740 | B1 | 1/2003 | Ashley et al. |
| 6,617,318 | B1 | 9/2003 | Nelson et al. |
| 6,624,168 | B2 | 9/2003 | Nelson et al. |
| 6,638,922 | B2 | 10/2003 | Ashley et al. |
| 6,642,270 | B2 | 11/2003 | Nelson et al. |
| 6,683,068 | B2 | 1/2004 | Nelson et al. |
| 6,818,634 | B2 | 11/2004 | Nelson et al. |
| 6,818,635 | B2 | 11/2004 | Nelson et al. |
| 6,833,365 | B2 | 12/2004 | Levy et al. |
| 6,841,546 | B2 | 1/2005 | Draper et al. |
| 6,846,939 | B2 | 1/2005 | Nelson et al. |
| 6,849,615 | B2 | 2/2005 | Nelson et al. |
| 6,894,036 | B2 | 5/2005 | Ashley et al. |
| 6,946,453 | B2 | 9/2005 | Ashley et al. |
| 7,001,918 | B2 | 2/2006 | Huss et al. |
| 7,045,507 | B2 | 5/2006 | Draper et al. |
| 7,056,902 | B2 | 6/2006 | Nelson et al. |
| 7,067,681 | B2 | 6/2006 | Nelson et al. |
| 7,094,806 | B2 | 8/2006 | Nelson et al. |
| 7,202,235 | B2 | 4/2007 | Levy et al. |
| 7,208,482 | B2 | 4/2007 | Garcia-Luzon et al. |
| 7,323,492 | B2 | 1/2008 | Huss et al. |
| 7,326,696 | B2 | 2/2008 | Nelson et al. |
| 7,361,674 | B2 | 4/2008 | Nelson et al. |
| 7,414,041 | B2 | 8/2008 | Levy |
| 7,521,437 | B2 | 4/2009 | Nelson et al. |
| 7,553,828 | B2 | 6/2009 | Nelson et al. |
| 8,088,755 | B2 | 1/2012 | Berniac et al. |
| 2002/0115644 | A1 | 8/2002 | Levy et al. |
| 2002/0128237 | A1 | 9/2002 | Nelson et al. |
| 2003/0069721 | A1 | 4/2003 | Podlogar |
| 2003/0195174 | A1 | 10/2003 | Ashley et al. |
| 2004/0013183 | A1 | 1/2004 | Bremer |
| 2004/0063674 | A1 | 4/2004 | Levy et al. |
| 2004/0067912 | A1 | 4/2004 | Hlavka et al. |
| 2004/0092490 | A1 | 5/2004 | Draper et al. |
| 2004/0138183 | A1 | 7/2004 | Nelson et al. |
| 2004/0157807 | A1 | 8/2004 | Levy |
| 2004/0176334 | A1 | 9/2004 | Nelson et al. |
| 2004/0214800 | A1 | 10/2004 | Levy et al. |
| 2004/0214801 | A1 | 10/2004 | Nelson et al. |
| 2004/0242548 | A1 | 12/2004 | Draper et al. |
| 2004/0266740 | A1 | 12/2004 | Huss et al. |
| 2005/0020545 | A1 | 1/2005 | Draper et al. |
| 2005/0026875 | A1 | 2/2005 | Nelson et al. |
| 2005/0026876 | A1 | 2/2005 | Nelson et al. |
| 2005/0038001 | A1 | 2/2005 | Attawia et al. |
| 2005/0038002 | A1 | 2/2005 | Nelson et al. |
| 2005/0070510 | A1 | 3/2005 | Draper et al. |
| 2005/0119235 | A1 | 6/2005 | Nelson et al. |
| 2005/0137174 | A1 | 6/2005 | Ohemeng et al. |
| 2005/0143352 | A1 | 6/2005 | Nelson et al. |
| 2005/0143353 | A1 | 6/2005 | Nelson et al. |
| 2005/0187198 | A1 | 8/2005 | Nelson et al. |
| 2005/0215532 | A1 | 9/2005 | Levy et al. |
| 2005/0245491 | A9 | 11/2005 | Hlavka et al. |
| 2005/0250744 | A1 | 11/2005 | Levy et al. |
| 2005/0267079 | A1 | 12/2005 | Hlavka et al. |
| 2005/0282787 | A1 | 12/2005 | Myers et al. |
| 2005/0288262 | A1 | 12/2005 | Bandarage et al. |
| 2006/0003971 | A1 | 1/2006 | Nelson |
| 2006/0084634 | A1 | 4/2006 | Huss et al. |
| 2006/0089336 | A1 | 4/2006 | Nelson et al. |
| 2006/0148765 | A1 | 7/2006 | Nelson et al. |
| 2006/0166944 | A1 | 7/2006 | Berniac et al. |
| 2006/0166945 | A1 | 7/2006 | Abato et al. |
| 2006/0166946 | A1 | 7/2006 | Nelson et al. |
| 2006/0194773 | A1 | 8/2006 | Levy et al. |
| 2006/0205698 | A1 | 9/2006 | Nelson et al. |
| 2006/0229282 | A1 | 10/2006 | Nelson et al. |
| 2006/0281717 | A1 | 12/2006 | Berniac et al. |
| 2006/0287283 | A1 | 12/2006 | Amoo et al. |
| 2007/0072834 | A1 | 3/2007 | Nelson et al. |
| 2007/0093455 | A1 | 4/2007 | Abato et al. |
| 2007/0155708 | A1 | 7/2007 | Nelson et al. |
| 2007/0155957 | A1 | 7/2007 | Alekshun et al. |
| 2007/0167415 | A1 | 7/2007 | Levy et al. |
| 2007/0270389 | A1 | 11/2007 | Garcia-Luzon et al. |
| 2008/0015169 | A1 | 1/2008 | Nelson et al. |
| 2008/0070873 | A1 | 3/2008 | Alekshun et al. |
| 2008/0118979 | A1 | 5/2008 | Draper et al. |
| 2008/0167273 | A1 | 7/2008 | Nelson et al. |
| 2008/0287401 | A1 | 11/2008 | Johnston et al. |
| 2008/0300424 | A1 | 12/2008 | Nelson et al. |
| 2008/0306032 | A1 | 12/2008 | Nelson et al. |
| 2009/0054379 | A1 | 2/2009 | Huss et al. |
| 2009/0118269 | A1 | 5/2009 | Berniac et al. |
| 2009/0124583 | A1 | 5/2009 | Nelson et al. |
| 2009/0131696 | A1 | 5/2009 | Levy |
| 2009/0156842 | A1 | 6/2009 | Seyedi et al. |

FOREIGN PATENT DOCUMENTS

| | | | |
|---|---|---|---|
| GB | 935384 | A | 8/1963 |
| WO | WO-9522529 | A1 | 8/1995 |
| WO | WO-01/52858 | | 7/2001 |
| WO | WO-2004/006850 | A2 | 1/2004 |
| WO | WO-2005/082860 | A1 | 9/2005 |
| WO | WO-2006084265 | A1 | 8/2006 |
| WO | WO-2007133797 | A2 | 11/2007 |
| WO | WO-2007133798 | A2 | 11/2007 |
| WO | WO-2008045507 | A2 | 4/2008 |
| WO | WO-2008079339 | A2 | 7/2008 |

OTHER PUBLICATIONS

Koza, Darrell J. et al., "Synthesis and Biological Evaluation of 9-Substituted Tetracycline Derivatives," Bioorganic & Medicinal Chemistry Letters, vol. 12:2163-2165 (2002).

Koza, Darrell J., "Synthesis of 7-Substituted Tetracycline Derivatives," Organic Letters, vol. 2(6):815-817 (2000).

Koza, Darrell J., "The synthesis of 8-substituted tetracycline derivatives, the first 8-position carbon-carbon bond," Tetrahedron Letters, vol. 41:5017-5020 (2000).

Martell, Michael J., Jr. et al., "The 6-Deoxytetracyclines. IX. Imidomethylation," J. Med. Chem., vol. 10(3):359-363 (1967).

Nelson et al., "Inhibition of the Tetracycline Efflux Antiport Protein by 13-Thio-Substituted 5-Hydroxy-6-deoxytetracylines".

Paemon, Liesbet et al., "The Gelatinase Inhibitory Activity of Tetracyclines and Chemically Modified Tetracycline Analogues as Measured by a Novel Microtiter Assay for Inhibitors," Biochemical Pharmacology, vol. 52:105-111 (1996).

Spencer, John L. et al., "6-Deoxytetracyclines. V. 7,9-Disubstituted Products," J. Med. Chem., vol. 122:404-407 (1963).

Sum, P.-E. et al., "Recent Developments in Tetracycline Antibiotics," Current Pharmaceutical Design, vol. 4(2):119-132 (1998).

Sum, Phaik-Eng et al., "Glycylcyclines. 1. A New Generation of Potent Antibacterial Agents through Modification of 9-Aminotetracyclines," J. Med. Chem., vol. 37:184-188 (1994).

Sum, Phaik-Eng et al., "Synthesis and antibacterial activity of 9-substituted minocycline derivatives," Bioorganic & Medicinal Chemistry Letters, vol. 16:400-403 (2006).

Sum, Phaik-Eng et al., "Synthesis and Structure-activity Relationship of Novel Gycylcycline Derivatives Leading to the Discovery of GAR-936," Bioorganic & Medicinal Chemistry Letters, vol. 9:1459-1462 (1999).

Tally, F.T. et al., "Glycylcydines: a new generation of tetracyclines," Journal of Antimicrobial Chemotherapy, vol. 35:449-452 (1995).

11A, 12-DERIVATIVES OF TETRACYCLINE COMPOUNDS

RELATED APPLICATIONS

This application is a continuation of U.S. application Ser. No. 11/348,608 (Allowed) filed Feb. 6, 2006, which claims the benefit of U.S. Provisional Application No. 60/650,031 filed Feb. 4, 2005, the entire contents of each of the aforementioned applications are incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and *Salmonella*). The rise of tetracycline-resistant organisms has resulted in a general decline in use of tetracyclines and tetracycline analogue compositions as antibiotics of choice.

SUMMARY OF THE INVENTION

In one embodiment, the invention pertains, at least in part, to 12-dehydrotetracycline compounds. In a further embodiment, the invention pertains to tetracycline compounds of formula (I):

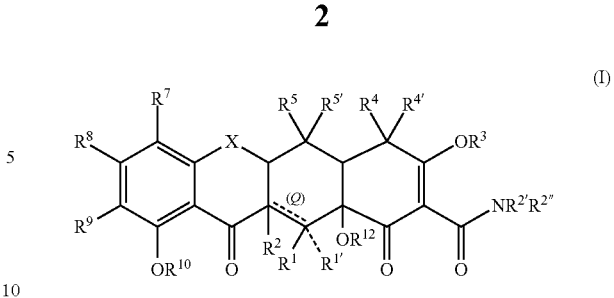

wherein
$R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen, optionally linked to $R^2$ to form a ring;

$R^2$ is hydrogen, alkyl, halogen, alkenyl, alkynyl, aryl, hydroxyl, thiol, cyano, nitro, acyl, formyl, alkoxy, amino, alkylamino, heterocyclic, or absent, optionally linked to $R^1$ to form a ring;

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, and $R^{12}$ are each hydrogen, alkyl, aryl, benzyl, arylalkyl, or a pro-drug moiety;

$R^4$ and $R^{4'}$ are each independently $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{7c})_{0-1}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}(NR^{8c})_{0-1}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{9c})_{0-1}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;
E' is O, $NR^{8f}$, or S;
Q is a double bond when $R^{1'}$ and $R^2$ are absent, Q is a single bond when $R^{1'}$ and $R^2$ are each independently hydrogen, alkyl, halogen, hydroxyl, thiol, alkenyl, alkynyl, aryl, acyl, formyl, alkoxy, amino, alkylamino, or heterocyclic;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^{6'}R^{6}$, S, $NR^{6}$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters, prodrugs, and enantiomers thereof.

In yet another embodiment, the invention pertains, at least in part, to tetracycline compound of formula (II):

(II)

wherein $R^{1}$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen;

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{3}$, $R^{10}$, and $R^{12}$ are each independently hydrogen, alkyl, aryl, benzyl, arylalkyl, or a pro-drug moiety;

$R^{4}$ is $NR^{4a}R^{4b}$, alkyl, alkenyl, alkynyl, hydroxyl, halogen, or hydrogen;

$R^{5}$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^{6}$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7}$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{7c})_{0-1}C(=W')WR^{7a}$;

$R^{8}$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}(NR^{8c})_{0-1}C(=E')ER^{8a}$;

$R^{9}$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{9c})_{0-1}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^{6'}R^{6}$, S, $NR^{6}$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

The invention also includes, for example, method for treating a tetracycline responsive state in a subject. The methods include administering to a subject an effective amount of a tetracycline compound of the invention (e.g., a compound of any one of formula I, II or otherwise described herein).

The invention also pertains, at least in part, to pharmaceutical compositions which comprise an effective amount of a tetracycline compound of the invention (e.g., a tetracycline compound of formula I, II, or otherwise described herein) and a pharmaceutically acceptable carrier.

The invention also pertains, at least in part, to a method for synthesizing dehydrotetracycline compounds. The method includes contacting a tetracycline compound with an effective amount of a reducing agent to form a 12-hydroxy tetracycline compound; and contacting the 12-hydroxy tetracycline compound with a dehydration agent, to form a dehydrotetracycline compound.

The invention also pertains, at least in part, to a method for synthesizing C11a-C12 cleaved tetracycline compounds, by contacting a dehydrotetracycline compound with a cleavage reagent, such that a C11a-C12 cleaved tetracycline compound is formed.

In another embodiment, the invention pertains to a method of synthesizing a substituted tetracycline compound, by contacting a dehydrotetracycline compound with a reactive agent, such that a substituted tetracycline compound is formed.

DETAILED DESCRIPTION OF THE INVENTION

1. Dehydrotetracycline Compounds

The invention pertains, at least in part, to novel 11a, and/or 12-position derivatives of tetracyclines and methods of producing 11a, 12-dehydrotetracycline compounds.

The term "tetracycline compound" includes many compounds with a similar ring structure to tetracycline. Examples of tetracycline compounds include: tetracycline, oxytetracycline, chlortetracycline, demeclocycline, doxycycline, chelocardin, minocycline, rolitetracycline, lymecycline, sancycline, methacycline, apicycline, clomocycline, guamecycline, meglucycline, mepylcycline, penimepicycline, pipacycline, etamocycline, and penimocycline. Other derivatives and analogues comprising a similar four ring structure are also included. The term includes 4-dedimethylamino derivatives. Table 1 depicts tetracycline and several known tetracycline derivatives. The tetracycline compounds may be unsubstituted at any position or further substituted, for example, at the 1, 2, 3, 4, 5, 6, 7, 8, 9, 10, 12a or 13 position of the ring. The C12 position on each of the tetracycline compounds shown in Table 1 is indicated by an arrow.

TABLE I

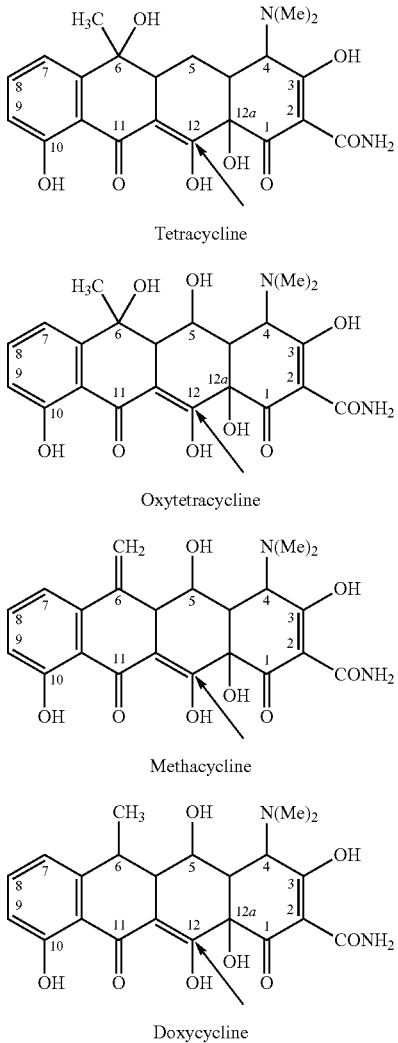

Tetracycline

Oxytetracycline

Methacycline

Doxycycline

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a C1-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a,6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a, 11a dehydro tetracyclines; 11a C1-6, 12 hemiketal tetracyclines; 11a C1-6-methylene tetracyclines; 6, 13 diol tetracyclines; 6-benzylthiomethylene tetracyclines; 7,11a-dichloro-6-fluoro-methyl-6-deoxy tetracyclines; 6-fluoro (α)-6-demethyl-6-deoxy tetracyclines; 6-fluoro (β)-6-demethyl-6-deoxy tetracyclines; 6-αacetoxy-6-demethyl tetracyclines; 6-β acetoxy-6-demethyl tetracyclines; 7,13-epithiotetracyclines; oxytetracyclines; 11a halogens of tetracyclines; 12a formyl and other esters of tetracyclines; 5, 12a esters of tetracyclines; 10,12a-diesters of tetracyclines; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines. Other examples of tetracycline compounds which may be used to form dehydrotetracycline compounds of the invention include those described in U.S. Published Applications 20040002481 and 20050282787, each incorporated herein by reference.

The term "12-dehydrotetracycline compounds" or "12-position tetracycline derivatives" includes tetracycline compounds which contain a substituent other than a hydroxy at the C12 position and/or a substitution at the 11a position. In an embodiment, the dehydrotetracycline compound is dehydrotetracycline (e.g., wherein $R^4$ is $NR^{4a}R^{4b}$; $R^{4a}$ and $R^{4b}$ are methyl, $R^{4'}$, $R^5$, and $R^{5'}$ are hydrogen and X is $CR^6R^{6'}$, wherein $R^6$ is methyl and $R^{6'}$ is hydroxy); dehydrodoxycycline (e.g., wherein $R^4$ is $NR^{4a}R^{4b}$; $R^{4a}$ and $R^{4b}$ are methyl, $R^5$ is hydroxyl, $R^{4'}$ and $R^{5'}$ are hydrogen, and X is $CR^6R^{6'}$, wherein $R^6$ is methyl and $R^{6'}$ is hydrogen); dehydrominocycline (wherein $R^4$ is $NR^{4a}R^{4b}$; $R^{4a}$ and $R^{4b}$ are methyl; $R^{4'}$, $R^{5'}$, and $R^5$ are hydrogen and X is $CR^6R^{6'}$ wherein $R^6$ and $R^{6'}$ are hydrogen atoms, and $R^7$ is dimethylamino); or dehydrosancycline (wherein $R^4$ is $NR^{4a}R^{4b}$; $R^{4a}$ and $R^{4b}$ are methyl; $R^{4'}$, $R^{5'}$, and $R^5$ are hydrogen and X is $CR^6R^{6'}$ wherein $R^6$ and $R^{6'}$ are hydrogen atoms. In one embodiment, $R^4$ and $R^{4'}$ are each hydrogen or the oxygen of a carbonyl group. The terms include compounds of formula (I) and (II).

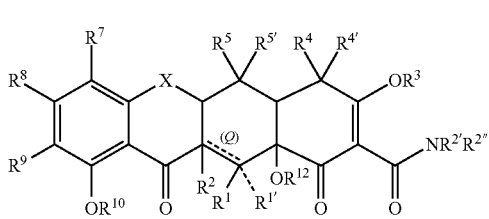

(I)

wherein $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen, optionally linked to $R^2$ to form a ring;

$R^2$ is hydrogen, alkyl, halogen, alkenyl, alkynyl, aryl, hydroxyl, thiol, cyano, nitro, acyl, formyl, alkoxy, amino, alkylamino, heterocyclic, or absent, optionally linked to $R^1$ to form a ring;

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, and $R^{12}$ are each hydrogen, alkyl, aryl, benzyl, arylalkyl, or a pro-drug moiety;

$R^4$ and $R^{4'}$ are each independently $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $—(CH_2)_{0-3}(NR^{7c})_{0-1}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $—(CH_2)_{0-3}(NR^{8c})_{0-1}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $—(CH_2)_{0-3}(NR^{9c})_{0-1}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

Q is a double bond when $R^{1'}$ and $R^2$ are absent, Q is a single bond when $R^{1'}$ and $R^2$ are each independently hydrogen, alkyl, halogen, hydroxyl, thiol, alkenyl, alkynyl, aryl, acyl, formyl, alkoxy, amino, alkylamino, or heterocyclic;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^6R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters, prodrugs, and enantiomers thereof.

In another embodiment, the invention pertains to tetracycline compounds of formula (II):

(II)

wherein $PR^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen; $PR^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety; $PR^3$, $R^{10}$, and $R^{12}$ are each independently hydrogen, alkyl, aryl, benzyl, arylalkyl, or a pro-drug moiety; $PR^4$ is $NR^{4a}R^{4b}$, alkyl, alkenyl, alkynyl, hydroxyl, halogen, or hydrogen; $PR^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy; $PR^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl; $PR^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $—(CH_2)_{0-3}(NR^{7c})_{0-1}C(=W')WR^{7a}$; $PR^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $—(CH_2)_{0-3}(NR^{8c})_{0-1}C(=E')ER^{8a}$; $PR^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $—(CH_2)_{0-3}(NR^{9c})_{0-1}C(=Z')ZR^{9a}$; $PR^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety; $PR^{13}$ is hydrogen, hydroxy, alkyl, alkenyl, alkynyl, alkoxy, alkylthio, aryl, alkylsulfinyl, alkylsulfonyl, alkylamino, or an arylalkyl; PE is $CR^{8d}R^{8e}$, S, $NR^{8b}$ or O; PE' is O, $NR^{8f}$, or S; PW is $CR^{7d}R^{7e}$, S, $NR^{7b}$ or O; PW' is O, $NR^{7f}$, or S; PX is $CHC(R^{13}Y'Y)$, $C=CR^{13}Y$, $CR^6R^6$, S, $NR^6$, or O; PY' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; PZ is $CR^{9d}R^{9e}$, S, $NR^{9b}$ or O; PZ' is O, S, or $NR^{9f}$, and pharmaceutically acceptable salts, esters and enantiomers thereof. PIn another embodiment, the tetracycline compound of formula I or II is a 12-dehydro sancycline compound, wherein $R^{2'}$, $R^3$, $R^{10}$, $R^{11}$ and $R^{12}$ are each hydrogen or a prodrug moiety; $R^4$ is $NR^{4a}R^{4b}$; $R^{4a}$ and $R^{4b}$ are each alkyl; X is $CR^6R^{6'}$; and $R^{2''}$, $R^{4'}$, $R^5$, $R^{5'}$, $R^6$, and $R^{6'}$ are each hydrogen. PIn another embodiment, the tetracycline compound of formula I or II, is a 12-dehydro tetracycline compound, wherein $R^4$ is $NR^{4a}R^{4b}$; $R^{4a}$ and $R^{4b}$ are each alkyl; $R^5$ and $R^{5'}$ are hydrogen and X is $CR^6R^{6'}$, wherein $R^6$ is methyl and $R^{6'}$ is hydroxy. PIn another embodiment, the tetracycline compound of formula I or II is a 12-dehydro doxycycline compound, wherein $R^4$ is $NR^{4a}R^{4b}$; $R^{4a}$ and $R^{4b}$ are each alkyl (e.g., methyl); $R^5$ is hydroxyl; X is $CR^6R^{6'}$; $R^6$ is methyl; and $R^{5'}$ and $R^{6'}$ are hydrogen. PIn another embodiment, the tetracycline compound of formula I or II is a 12-dehydro minocycline compound, wherein $R^4$ is $NR^{4a}R^{4b}$; $R^{4a}$ and $R^{4b}$ are each alkyl (e.g., methyl); X is $CR^6R^{6'}$; $R^5$, $R^{5'}$, $R^6$ and $R^{6'}$ are hydrogen atoms and $R^7$ is dimethylamino. PIn an embodiment, the invention pertains to tetracycline compounds of formula I or II, wherein $R^1$ is hydrogen, halogen (e.g., fluorine, chlorine, bromine, iodine, etc.), hydroxy, thiol, amino, cyano, acyl, alkoxy, carboxyl, amido, alkyl, alkenyl, alkynyl, aryl, heterocyclic, alkylamino, or any other substituent which allows the tetracycline compound to perform its intended function. PIn another embodiment, the invention pertains to tetracycline compounds of formula I, wherein Q is a single bond. When Q is a single bond, the invention pertains to tetracycline compounds wherein $R^2$ is hydrogen, halogen, cyano, alkyl, hydroxy, alkoxy, or any other substituent which allows the compounds of the invention to perform their intended function. In one particular embodiment, the invention pertains to compounds wherein Q is a single bond, and $R^1$, $R^{1'}$ and $R^2$ are each independently hydrogen. In another embodiment, the invention pertains to tetracycline compounds of formula I, wherein Q is a double bond. In another embodiment, the invention pertains to tetracycline compounds wherein $R^1$ and $R^2$ are linked to form a ring. In one embodiment, $R^1$ and $R^2$ are linked to form an epoxide, a lactam, a lactone, a carboxylic ring, a heterocyclic ring, or other ring structure. In one embodiment, $R^1$ and $R^2$ are linked to form a 3, 4, 5, 6, 7, 8, or 9 membered ring. PIn a further embodiment, $R^9$ is hydrogen. In another embodiment, $R^9$ is substituted or unsubstituted aryl (e.g., substituted or unsubstituted carbocyclic, e.g., phenyl or naphthyl; or substituted or unsubstituted heteroaryl). $R^9$ also may be substituted or unsubstituted alkenyl or substituted or unsubstituted alkynyl. $R^9$ also may be heterocyclic or alkylcarbonyl, alkenylcarbonyl, alkynylcarbonyl, alkyloxycarbonyl, or otherwise comprise a substituted carbonyl, acyl, acetyl, or formyl moiety. PIn another further embodiment, $R^9$ is substituted or unsubstituted alkyl. In a further embodiment, $R^9$ is aminoalkyl, e.g., aminomethyl. In a further embodiment, the aminoalkyl is further substituted with any substituent which allows the compound to perform its intended function. In a further embodiment, the aminoalkyl substituent is alkylaminomethyl. PIn another further embodiment, $R^9$ is substituted or unsubstituted amino, e.g., alkylamino, dialkylamino, arylamino, alkylcarbonylamino, alkylaminocarbonyl amino, arylcarbonylamino, etc. In another embodiment, $R^9$ is amido. In yet another embodiment, $R^9$ is cyano, halogen (e.g., fluorine, bromine, chlorine, iodo, etc.), nitro, hydroxyl, alkoxy, or any other substituent which allows the tetracycline compound to perform its intended function. In another embodiment, $R^9$ is an $R^9$ moiety described in WO 03/079984; WO 03/075857; WO 02/04406; or WO 01/74761, incorporated herein by reference in its entirety.

In a further embodiment, $R^7$ is hydrogen. In another embodiment, $R^7$ is substituted or unsubstituted aryl (e.g., substituted or unsubstituted carbocyclic, e.g., phenyl or naphthyl; or substituted or unsubstituted heteroaryl). $R^7$ also may be substituted or unsubstituted alkenyl or substituted or unsubstituted alkynyl. $R^7$ also may be heterocyclic or alkylcarbonyl, alkenylcarbonyl, alkynylcarbonyl, alkyloxycarbonyl, or otherwise comprise a substituted carbonyl, acyl, acetyl, or formyl moiety.

In another further embodiment, $R^7$ is substituted or unsubstituted alkyl. In a further embodiment, $R^7$ is aminoalkyl, e.g., aminomethyl. In a further embodiment, the aminoalkyl is further substituted with any substituent which allows the compound to perform its intended function. In a further embodiment, the aminoalkyl substituent is alkylaminomethyl.

In another embodiment, $R^7$ is substituted or unsubstituted amino, e.g., alkylamino, dialkylamino, arylamino, alkyl carbonylamino, alkyl aminocarbonylamino, arylcarbonylamino, etc. In another embodiment, $R^7$ is amido. In yet another embodiment, $R^7$ is cyano, halogen (e.g., fluorine, bromine, chlorine, iodo, etc.), nitro, hydroxyl, alkoxy, or any other substituent which allows the tetracycline compound to perform its intended function. In another embodiment, $R^7$ is a 7-position moiety described in WO 02/04407, WO 01/74761, WO 03/079984, or WO 03/075857, incorporated herein by reference in their entirety.

In a further embodiment, $R^8$ is hydrogen. In another embodiment, $R^8$ is substituted or unsubstituted aryl (e.g., substituted or unsubstituted carbocyclic, e.g., phenyl or naphthyl; or substituted or unsubstituted heteroaryl). $R^8$ also may be substituted or unsubstituted alkenyl or substituted or unsubstituted alkynyl. $R^8$ also may be heterocyclic or alkylcarbonyl, alkenylcarbonyl, alkynylcarbonyl, alkyloxycarbonyl, or otherwise comprise a substituted carbonyl, acyl, acetyl, or formyl moiety.

In another further embodiment, $R^8$ is substituted or unsubstituted alkyl. In a further embodiment, $R^8$ is aminoalkyl, e.g., aminomethyl. In a further embodiment, the aminoalkyl is further substituted with any substituent which allows the compound to perform its intended function. In a further embodiment, the aminoalkyl substituent is alkylaminomethyl.

In another embodiment, $R^8$ is substituted or unsubstituted amino, e.g., alkylamino, dialkylamino, arylamino, alkyl carbonylamino, alkylaminocarbonyl amino, arylcarbonylamino, etc. In another embodiment, $R^8$ is amido. In yet another embodiment, $R^8$ is cyano, halogen (e.g., fluorine, bromine, chlorine, iodo, etc.), nitro, hydroxyl, alkoxy, or any other substituent which allows the tetracycline compound to perform its intended function. In another embodiment, $R^8$ is an $R^8$ moiety described in WO 02/12170, WO 02/04404, or WO 03/079984, incorporated herein by reference in their entirety.

In another embodiment, $R^3$, $R^{10}$, and $R^{12}$ are each independently hydrogen, alkyl, acyl, aryl, or arylalkyl. Other $R^3$, $R^{10}$, and $R^{12}$ moieties are described in U.S. Ser. No. 10/619,653, incorporated herein by reference in its entirety. Other examples of $R^{2'}$ and $R^{2''}$ moieties are described in U.S. Published Application 20040002481.

In one embodiment, the tetracycline compound is a 12-dehydrodoxycycline compound of the formula:

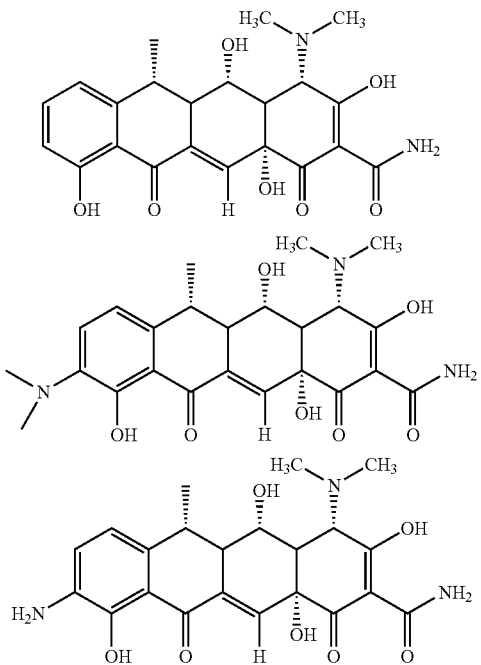

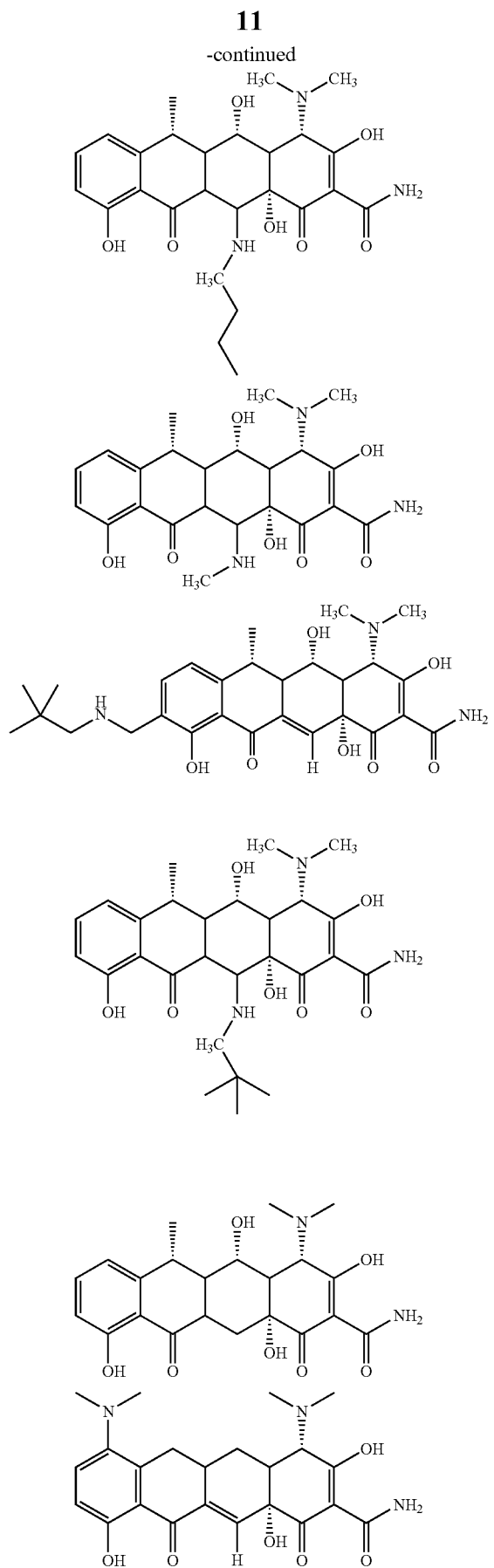
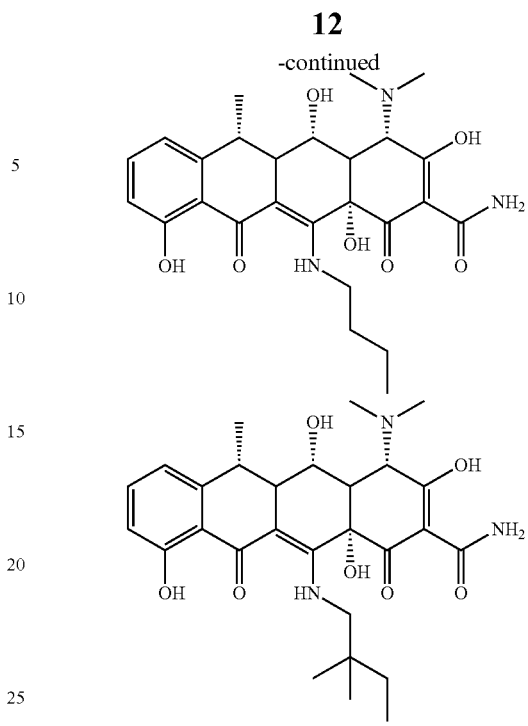

or a pharmaceutically acceptable salt, ester or prodrug thereof.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl(benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxophenyl, quinoline, isoquinoline, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl(alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" or "alkyl aminoalkyl" refers to an alkyl, alkenyl, or alkynyl group bound to a nitrogen atom which is also bound to an alkyl group.

The term "amide" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo and moieties which may advantageously remain esterified or otherwise protected in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino loweralkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

2. Methods for Synthesizing 11a, 12-Dehydrotetracycline Compounds

A method for derivatizing tetracycline compounds at the 11a and 12 positions has been discovered through chemical modification via reduction of C1 keto-enolate to produce a C12 hydroxyl group. The hydroxyl group is dehydrated to produce C11a-C12 dehydrotetracyclines with a reactive α,β-unsaturated carbonyl functional group, as shown in Scheme 1:

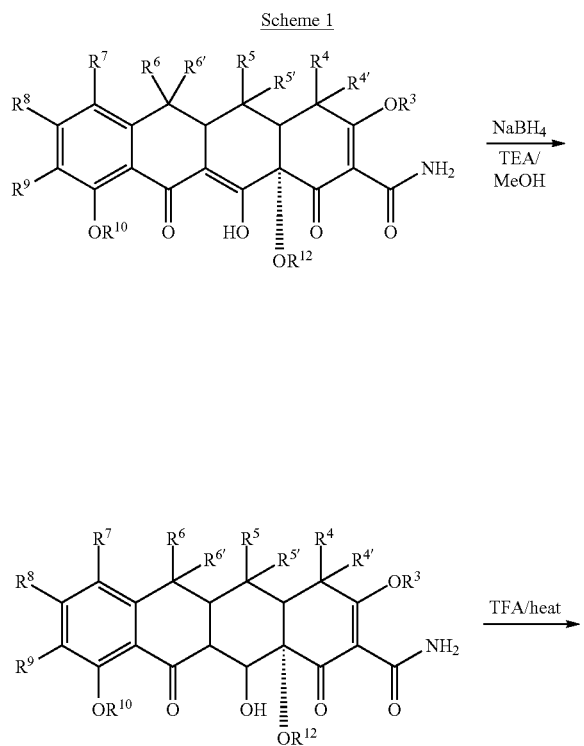

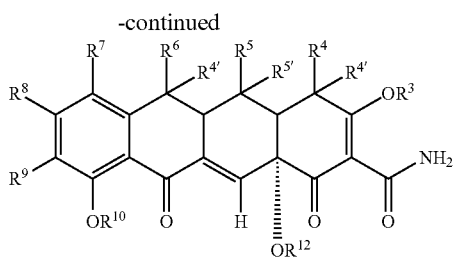

In one embodiment, the invention pertains to a method for synthesizing 11a,12-dehydrotetracycline compounds. The method includes contacting a tetracycline compound with an effective amount of a reducing agent to form a 11a, 12-hydroxy tetracycline compound, and contacting the 11a, 12-hydroxy tetracycline compound with a dehydration agent, such that a 11a, 12-dehydrotetracycline compound is formed.

The term "reducing agent" includes agents which are capable of reducing the C12 keto-enolate to a hydroxyl group. Examples of reducing agents are described in Comprehensive Organic Transformations ("COT") $2^{nd}$ Ed., Larock, 304, 305. In one embodiment, the reducing agent is sodium borohydride.

Dehydration agents are also known in the art. Examples of dehydration agents are described in Comprehensive Organic Transformations ("COT") $2^{nd}$ Ed., Larock, 304, 305, incorporated herein by reference. In one embodiment, the dehydration agent is an acid, e.g., trifluoroacetic acid and/or heat.

In one embodiment, the tetracycline compound is tetracycline, doxycycline, methacycline, minocycline, or sancycline. In another embodiment, the tetracycline compound is a tetracycline compound described in, for example, WO 03/079983, WO 02/12170, WO 02/04407, WO 02.04406, WO 02/04405, WO 02/04404, WO 01/74761, WO 03/079984, WO 03/075857, WO 03/057169, WO 02/072545, WO 02/072506, U.S. Ser. No. 10/619,653, U.S. Ser. No. 09/895,857; U.S. Ser. No. 09/895,812; U.S. Pat. No. 5,326, 759; U.S. Pat. No. 5,328,902; U.S. Pat. No. 5,495,031; U.S. Pat. No. 5,495,018; U.S. Pat. No. 5,495,030; U.S. Pat. No. 5,495,032; U.S. Pat. No. 5,512,553; U.S. Pat. No. 5,675,030; U.S. Pat. No. 5,843,925; U.S. Pat. No. 5,886,175; U.S. Pat. No. 6,165,999; U.S. Pat. No. 3,239,499; WO 95/22529; U.S. Pat. No. 5,064,821; U.S. Pat. No. 5,589,470; U.S. Pat. No. 5,811,412, U.S. Publication No. 20040002481, or U.S. Publication No. 20050282787, each of which is hereby incorporated by reference.

A wide range of tetracycline compounds of the invention can be synthesized using the methods of the invention. The tetracycline compounds of the invention can be synthesized, for example, by reacting various reactive agent, such as nucleophiles, with the dehydrotetracycline to produce tetracycline compounds of the invention. Examples of some of the substituted tetracyclines which can be synthesized using the methods of the invention include compounds with C12-carbon-carbon, C12-carbon-nitrogen and C12-carbon-oxygen or C12-carbon-heteroatom bonds at the $R^1$ position, as shown in Scheme 2.

Scheme 2

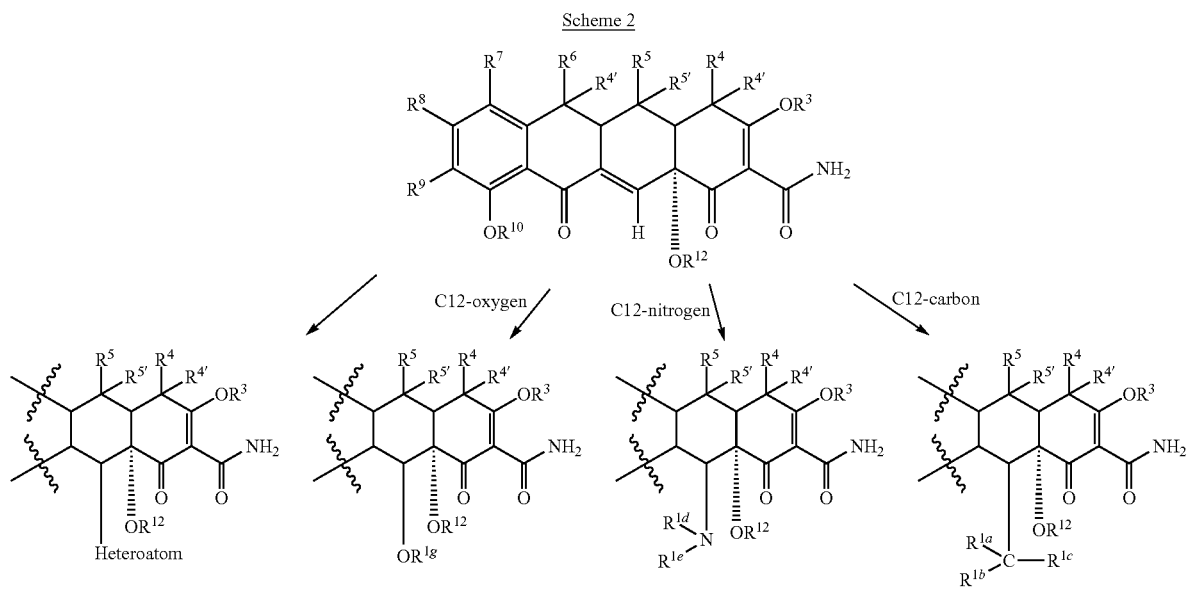

In Scheme 2, $R^{1a}$, $R^{1b}$, $R^{1c}$, $R^{1d}$, $R^{1e}$, and $R^{1g}$ are each independently hydrogen, alkyl, heterocyclic, aryl, alkenyl, alkynyl, alkoxy, carbonyl, acyl, halogen, cyano, amino, amido, nitro, or any other substituent described herein which would allow the tetracycline compounds of the invention to perform their intended functions.

Tetracycline compounds of the invention can be synthesized using methods and reactive agents known the art to react with α,β-unsaturated ketones. For example, anions, carbanions and alkali metals are reactive agents which react to give tetracycline compounds of the invention with various $R^1$ substituents (Scheme 3). Other reactive agents which can be used to synthesize the compounds of the invention with various $R^1$ substituents include alkali metal acetylides, lithium dialkyl cuprates, lithium diarylcuprates with or without complexing ligands. Tetracycline compounds with $R^1$ substituents can also be formed using reactive agents such as anions, e.g., anions generated from ketones, aldehydes and the like. Reactive agents also include organometallic reagents such as Grignards and organolithium and ylide reagents (COT, 351-401, Scheme 3).

Scheme 3

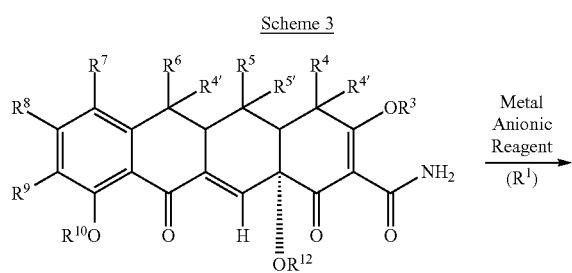

-continued

Other reactive agents which can be used include those used in enol-ester (COT, 1485-1487) and enol silane (COT, 1488-1505) reactions. Other reactive agents include hydration agents. Hydration can be used to introduce $R^1$ hydroxyl groups (COT, 991-995). Tetracycline compounds of the invention wherein $R^1$ is hydroxyl can be formed also by hydroboration followed by oxidation to an alcohol (COT, 1005-1008). The tetracycline compounds having a substituted carbonyl at the $R^1$ position can be synthesized by carbonylation (COT, 1009-1011, 1690-1693).

Tetracycline compounds of the invention having alkyl and other substituents at the $R^1$ position can be synthesized using a variety of reactive agents via free radical, Michael and Michael-like addition reactions, and organoboron reactions. Other possible reactive agents include catalysts which can be used to synthesize various tetracycline compounds of the invention include aluminum, gallium, thallium, silicon, germanium, tin, lead, stilbine, titanium, zirconium, manganese, iron, cobalt, rhodium, nickel, palladium, copper, silver, zinc, mercury, and others (COT, 1560-1616). Tetracycline compounds of the invention wherein $R^1$ is cyano can also be formed using reactive agents (COT, 1705-1706). Tetracycline compounds of the invention wherein $R^1$ is an ester can be synthesized, for example, using ester additions (COT, 1724-1725). Tetracycline compounds of the invention wherein $R^1$ comprises a nitrile group can be synthesized using nitrile addition reagents (COT, 1800-1801) as the reactive agent. Tetracycline compounds wherein $R^1$ is a formyl or other carbonyl group can be synthesized using hydroformylation reagents (COT, 1363-1380) as the reactive agent.

Tetracycline compounds of the invention wherein $R^1$ is an amide can be synthesized via amide conjugations (COT, 1701).

Scheme 4

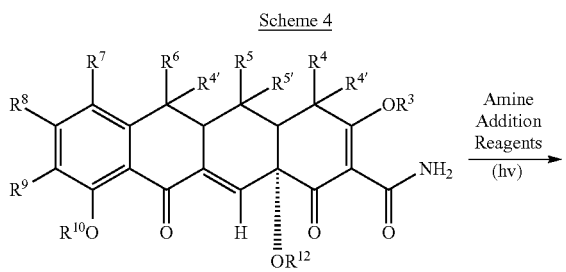

Tetracycline compounds of the invention include compounds wherein $R^1$ is an primary, secondary, or tertiary amine. Examples of reactive agents include primary and secondary amines. Amines can be formed using techniques known in the art (COT, 761-778). Tetracycline compounds of the invention with an amino $R^1$ substituent may also be used to form prodrugs based upon their reactivity with prodrug-forming reactive agents.

Tetracycline compounds of formula I, wherein Q is a double bond and $R^1$ is alkyl, alkenyl, alkynyl, or aryl can be synthesized using, for example, conjugate addition reactive agents as shown in Scheme 5 (COT, 1806-1841).

Scheme 5

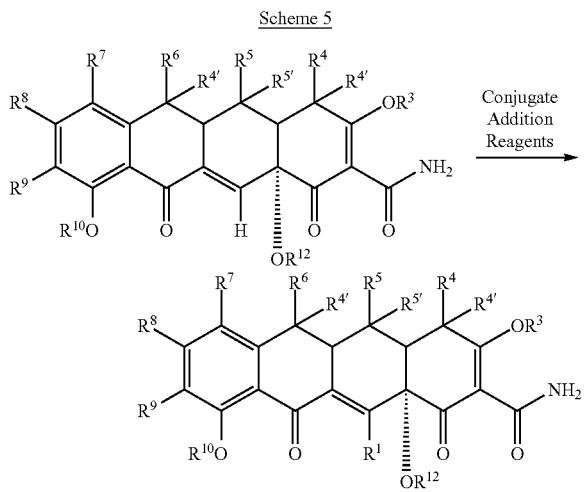

Tetracycline compounds of the invention wherein $R^2$ is alkyl, alkenyl, alkynyl, aryl, etc. can be synthesized, for example, using a variety of reactive agents such as metal anionic reagents (Scheme 6) and by the alkylation of enones (COT, 1546-1557).

Scheme 6

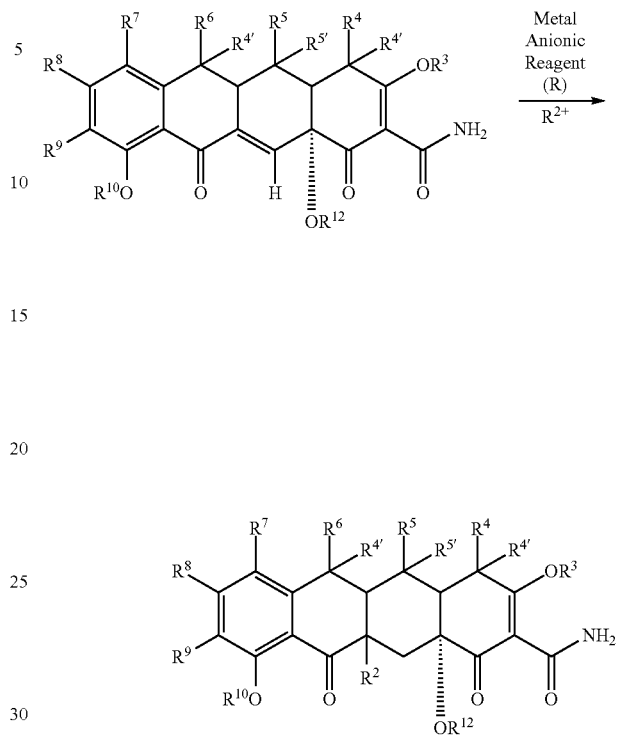

Tetracycline compounds wherein $R^2$ is hydroxy or a carbonyl group may be synthesized using asymmetric hydroboration (COT, 1008).

Tetracycline compounds of the invention may also be formed using reactions such as reductions via catalytic hydrogenation, selective hydrogenation, enantioselective hydrogenation, hydroboration-protonolysis, conjugate reduction, reduction dimerization (COT $2^{nd}$ Ed., Larock, pg 7-29), and coupling reactions (COT, 81).

Other tetracycline compounds of the invention wherein Q is a single bond, can be synthesized using a variety of reactive agents such as organosilicon reagents (COT, 108), organozirconium reagents (COT, 114), organonickel reagents (COT, 116-117), and organomercury (COT, 124) reagents.

Tetracycline compounds of the invention wherein $R^1$ and $R^2$ are halogens can be formed by, for example, halogen addition reactions (COT, 629-647). Tetracycline compounds of the invention wherein $R^1$ is alkyl and $R^2$ is halogen can be formed, for example, by haloalkylation reactions (COT, 647-653). Tetracycline compounds of the invention wherein $R^1$ and $R^2$ are hydroxyl can be synthesized by, for example, cis-hydroxylation (COT, 996-1001) and transhydroxylation (COT, 1001-1003).

Tetracycline compounds of the invention wherein $R^1$ and $R^2$ are carboxylate, alkyloxycarbonyl, aryloxycarbonyl, acetyl, hydroxyl, etc. can be synthesized using, for example, solvomercuration and demercuration (COT, 1629-1632) reactions (Scheme 7).

Scheme 7

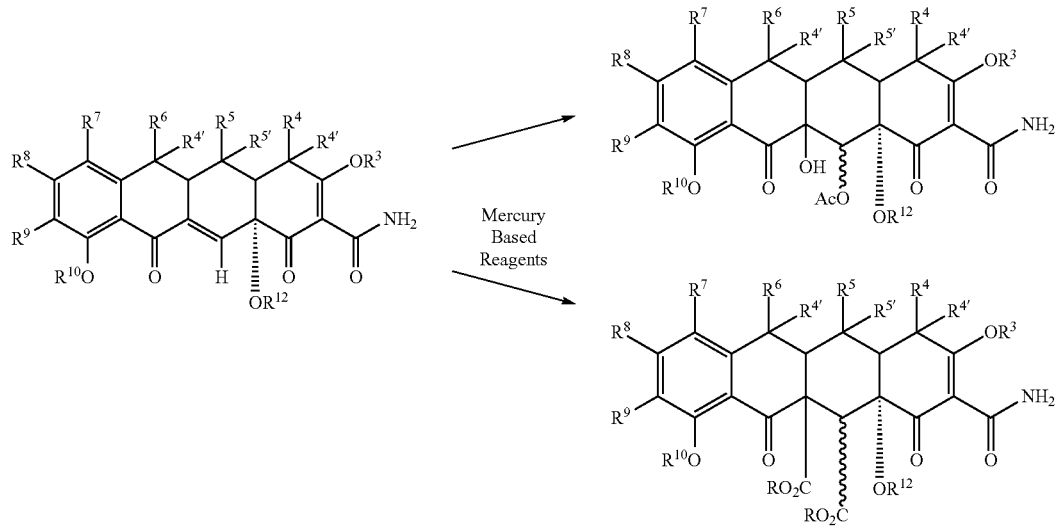

In a further embodiment, the invention pertains to methods for synthesizing C11a-C12 cleaved tetracycline compounds, by contacting a dehydrotetracycline compound with a cleavage reagent, such that C11a-C12 cleaved tetracycline compounds are formed. Examples of C11a-C12 cleaved tetracycline compounds include compounds of formula II. Cleavage and ozonolysis reagents are described in COT 1210-1215, and 1630-1634.

Tetracycline compounds of the invention wherein $R^1$ and $R^2$ are linked to form a ring can be synthesized by reacting the alkene to form a heterocycle such as a lactone or lactam (COT, 1876-1904), as shown in Scheme 8. Tetracycline compounds of the invention wherein $R^1$ and $R^2$ are linked to form an epoxide are also included (COT, 915-927).

Scheme 8

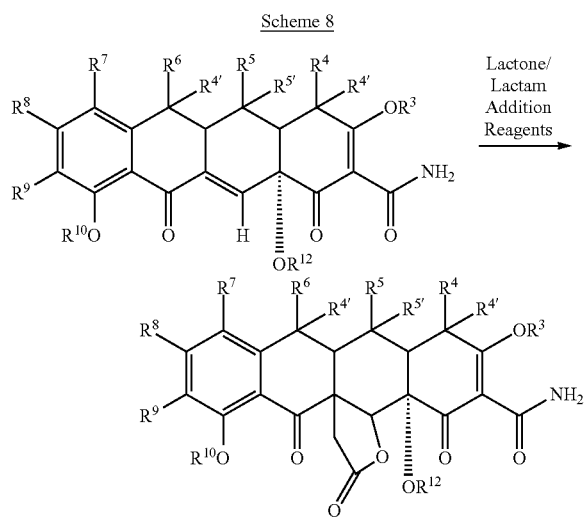

Tetracycline compounds of the invention also include compounds wherein $R^1$ and $R^2$ are linked to form rings with 3 (COT, 135) or more (COT, 136-186) members. Tetracycline compounds of the invention wherein $R^1$ and $R^2$ are linked to form a ring can also be synthesized via Diels-Alder reactions (COT 537), as well as other cyclization, reactions with ketenes (COT, 1340-1345), annulations (COT, 1345-1362) and related reactions (COT, 537-560). Other ring forming reactions which can be used to synthesize compounds of the invention include alkene additions using hv or boron reagents forming oxetanes and higher member rings (COT, 913-914, Scheme 6).

Scheme 9

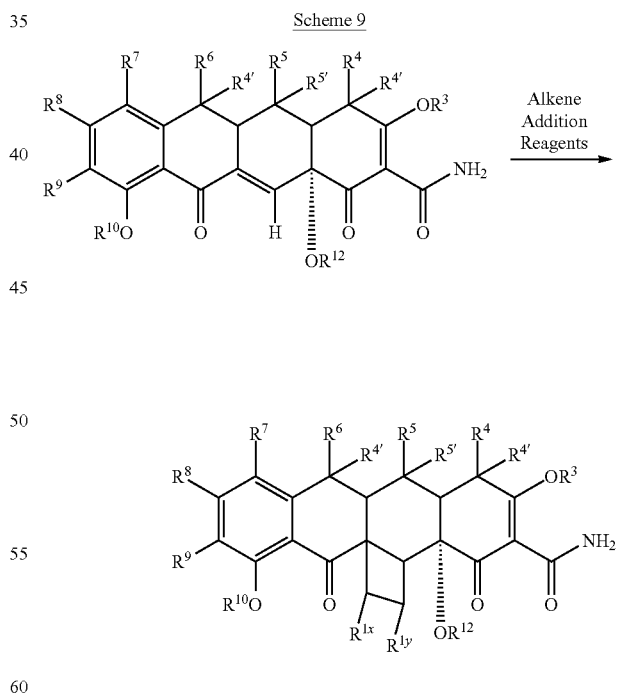

The tetracycline compounds of the invention also include tetracycline compounds with substituents at the 3, 4, 5, 6, 7, 8, 9, 10, 11, 12, etc. positions. For example in Scheme 10, a 11a, 12-dehydro doxycycline is substituted at the $R^9$ position with an amino functional group. This compound retains activity in inflammation models. Scheme 10 shows the derivatization of a 11a,12-dehydrotetracycline compound at the 9 position.

Scheme 10

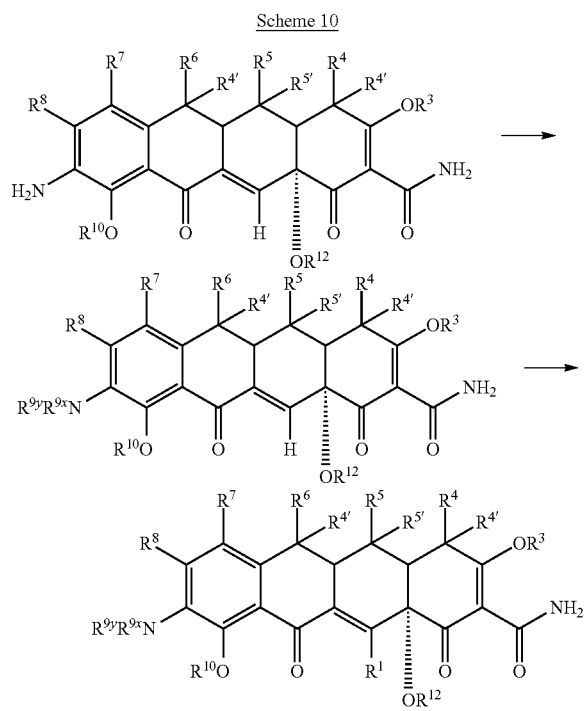

Tetracycline compounds of the invention also include compounds in which the non-aromatic double bond (e.g., Q) is contacted with a hydrogenating agent (Scheme 11). Suitable hydrogenating agents include, for example, hydrogen in combination with an appropriate catalyst, borohydride reagents, an aluminum hydride reagents and hydride salts (COT, 5-17).

Scheme 11

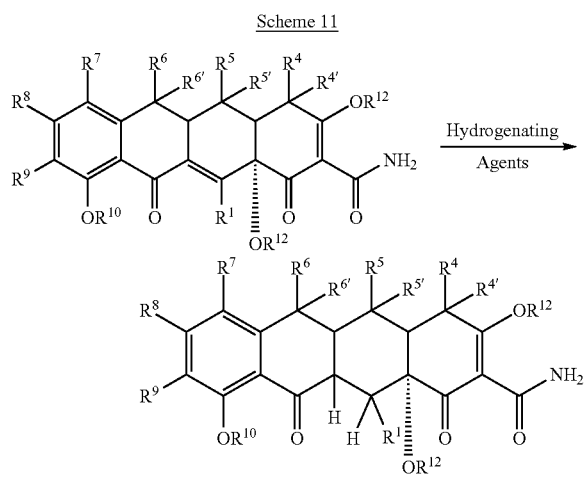

Examples of reactions which can be used, in part, to synthesize portions of the dehydrotetracycline compounds of the invention include those described in, for example, WO 03/079983, WO 02/12170, WO 02/04407, WO 02.04406, WO 02/04405, WO 02/04404, WO 01/74761, WO 03/079984, WO 03/075857, WO 03/057169, WO 02/072545, WO 02/072506, U.S. Ser. No. 10/619,653, U.S. Ser. No. 09/895,857; U.S. Ser. No. 09/895,812; U.S. Pat. No. 5,326,759; U.S. Pat. No. 5,328,902; U.S. Pat. No. 5,495,031; U.S. Pat. No. 5,495,018; U.S. Pat. No. 5,495,030; U.S. Pat. No. 5,495,032; U.S. Pat. No. 5,512,553; U.S. Pat. No. 5,675,030; U.S. Pat. No. 5,843,925; U.S. Pat. No. 5,886,175; U.S. Pat. No. 6,165,999; U.S. Pat. No. 3,239,499; WO 95/22529; U.S. Pat. No. 5,064,821; U.S. Pat. No. 5,589,470; U.S. Publication No. 2005/0282787; and U.S. Pat. No. 5,811,412, all incorporated herein by reference. In an embodiment, the present invention also pertains to 11a,12-dehydro derivatives of each of the tetracycline compounds disclosed in each of the above references.

In another embodiment, the invention pertains to tetracycline compounds synthesized by the methods described herein.

3. Methods for Using Dehydrotetracycline Compounds

The invention also pertains to methods for treating a tetracycline responsive states in subjects, by administering to a subject an effective amount of a tetracycline compound of the invention (e.g., a compound of Formula I, II, or otherwise described herein), such that the tetracycline responsive state is treated.

The term "treating" includes curing as well as ameliorating at least one symptom of the state, disease or disorder, e.g., the tetracycline compound responsive state.

The language "tetracycline compound responsive state" or "tetracycline responsive state" includes states which can be treated, prevented, or otherwise ameliorated by the administration of a tetracycline compound of the invention, e.g., a tetracycline compound of formula I, II or otherwise described herein). Tetracycline compound responsive states include bacterial, viral, parasitic, and fungal infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., Cancer Res., 48:6686-6690 (1988)). In a further embodiment, the tetracycline responsive state is not a bacterial infection. In another embodiment, the tetracycline compounds of the invention are essentially non-antibacterial. For example, non-antibacterial tetracycline compounds of the invention may have MIC values greater than about 4 µg/ml (as measured by assays known in the art and/or the assay given in Example 2). The tetracycline responsive state also may be one treatable by the administration of antioxidants.

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents.

Acute inflammation is short-lasting, lasting only a few days. If it is longer lasting however, then it may be referred to as chronic inflammation.

IPAF's include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, acne; sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention, e.g., a compound of formula I, II, or otherwise described herein. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease & Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states characterized by aberrant amounts of MMPs or MMP activity. These are also include as tetracycline compound responsive states which may be treated using compounds of the invention, e.g., a tetracycline compound of formula I, II, or otherwise described herein.

Examples of matrix metalloproteinase associated states ("MMPAS's") include, but are not limited to, arteriosclerosis, corneal ulceration, emphysema, osteoarthritis, multiple sclerosis (Liedtke et al., Ann. Neurol. 1998, 44:35-46; Chandler et al., J. Neuroimmunol. 1997, 72:155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., Annu. Rev. Cell Biol. 1993, 9:541-73; Tryggvason et al., Biochim. Biophys. Acta 1987, 907:191-217; Li et al., Mol. Carcinog. 1998, 22:84-89)), metastasis, acute lung injury, stroke, ischemic, diabetes, aortic or vascular aneurysms, skin tissue wounds, dry eye, bone and cartilage degradation (Greenwald et al., Bone 1998, 22:33-38; Ryan et al., Curr. Op. Rheumatol. 1996, 8; 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

In one embodiment, the tetracycline compounds of the invention are antioxidants. The term "antioxidant" refers to compounds that may protect cells from the damage caused by unstable molecules, such as free radical molecules. Free radical moieties lead to the oxidation of tissue resulting in, for example, aging, cancer, heart disease and the like. Without being bound to any particular theory, antioxidants may prevent free radicals from oxidizing sensitive biological molecules found in tissues and/or reduce the formation of free radicals.

Examples of tetracycline responsive states also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, demyelination-related disorders, senile dementia, Huntington's disease, Gilles de la Tourette's syndrome, multiple sclerosis (e.g., including but not limited to, relapsing and remitting multiple sclerosis, primary progressive multiple sclerosis, and secondary progressive multiple sclerosis), amylotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity. Further neurological disorders include, for example, those listed in the American Psychiatric Association's Diagnostic and Statistical manual of Mental Disorders (DSM), the most current version of which is incorporated herein by reference in its entirety.

In one embodiment, the tetracycline responsive state is a demyelination related disorder. The term "demyelination-related disorders" includes disorders which are associated with, caused by, or result in demyelination. Demyelination is a major underlying factor responsible for the symptoms of multiple sclerosis. Demyelination is the destructive removal of myelin, an insulating and protective fatty protein which sheaths the long extensions of neurons called axons. During relapses of multiple sclerosis, patches of white matter in the central nervous system that normally contain tracts of myelinated neurons become inflamed and lose their myelin. These patches of demyelination are known as lesions.

Not to be bound by theory, but it is believed that the body's own immune system is at least partially responsible. Acquired immune system cells, called T-cells, are known to be present at the site of lesions. Other immune system cells called macrophages (and possibly mast cells as well) also contribute to the damage.

Myelin is produced by oligodendrocytes in the central nervous system. One oligodendrocyte produces myelin for several axons and one axon has several oligodendrocytes producing its myelin. In multiple sclerosis, not only is the myelin destroyed but also the oligodendrocytes and even the axons themselves.

Axons use an electrochemical mechanism to transmit nerve impulses—the action potential. This requires sodium and potassium ions to pass through a semi-permeable membrane around the nerve. It is believed that the myelin not only insulates and encases this electrochemical process but also actively assists it. When axons become demyelinated, they transmit the nerve impulses 10 times slower than normal myelinated cells.

The term "demyelination-related disorder" includes multiple sclerosis, central pontine myelinolysis, leukodystrophies, acute disseminated encephalomyelitis, progressive multifocal leukoencephalopathy, subacute sclerosing panencephalitis, and other disorders caused or characterized by demyelination of neurons.

The term "multiple sclerosis" includes all forms of multiple sclerosis. It includes relapsing and remitting multiple sclerosis, primary progressive multiple sclerosis, and secondary progressive multiple sclerosis.

The language "in combination with" another therapeutic agent or treatment includes co-administration of the tetracycline compound and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent who is known in the art to treat, prevent, or reduce the symptoms of an IPAS and another tetracycline responsive state. Furthermore, the other therapeutic agent may be any agent of benefit to the patient when administered in combination with the administration of an tetracycline compound. In one embodiment, the cancers treated by methods of the invention include those described in U.S. Pat. Nos. 6,100,248; 5,843,925; 5,837,696; or 5,668,122, incorporated herein by reference in their entirety.

In another embodiment, the tetracycline compound responsive state is diabetes, e.g., juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a substituted tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited, to asthma, cystic fibrosis, and emphysema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, or ischemic stroke. The invention also pertains to a method for treating ischemia, stroke, or ischemic stroke by administering an effective amount of a substituted tetracycline compound of the invention. In a further embodiment, the tetracycline compounds of the invention are used to treat such disorders as described in U.S. Pat. No. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucusae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gellatinolytic activity of MMPs. In a further embodiment, the tetracycline compound of the invention is administered to the surface of the skin (e.g., topically). In a further embodiment, the tetracycline compound of the invention used to treat a skin wound, and other such disorders as described in, for example, U.S. Pat. Nos. 5,827,840; 4,704,383; 4,935,412; 5,258,371; 5,308,839I 5,459,135; 5,532,227; and 6,015,804; each of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention may be useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards, Document M7-A2*, vol. 10, no. 8, pp. 13-20, $2^{nd}$ edition, Villanova, Pa. (1990). In one embodiment, the tetracycline compounds are non-anti-bacterial (e.g., exhibit an MIC greater than about 8 μg/mL, as described in Example 2).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier. The tetracycline compounds of the invention may also be used to treat fungal disorders, viral disorders, parasitic disorders, and other disorders described in WO 03/005971, WO 02/085303, WO 02/072022, WO 02/072031, WO 01/52858, and U.S. Ser. No. 10/692,764, each of which is incorporated herein by reference in its entirety.

In another embodiment, the tetracycline responsive state is a disorder treated by modulation of RNA.

The term "disorders treatable by modulation of RNA" or "DTMR" includes viral, neurodegenerative and other disorders which are caused or related to RNA function, structure, amounts and/or other activities of RNA which are lower or higher than desired and those disorders treatable by compounds described herein. Examples of DTMR include viral disorders (e.g., retroviral disorders (e.g., HIV, etc.), disorders caused by human rhinovirus RNA and proteins, VEE virus, Venezuelan equine encephalitis virus, eastern X disease, West Nile virus, bacterial spot of peach, camelpox virus, potato leafroll virus, stubborn disease and infectious variegations of citrus seedlings, viral protein synthesis in *Escherichia coli* infected with coliphage MS2, yellow viruses, citrus greening disease, ratoon stunting disease, European yellows of plants, inclusion conjunctivitis virus, meningopneumonitis virus, trachoma virus, hog plague virus, ornithosis virus, influenza virus, rabies virus, viral abortion in ungulates, pneumonitis, and cancer.

Other exemplary DTMRs include disorders caused by, or associated with splicing. For example, some disorders associated with defects in pre-mRNA processing result from a loss of function due to mutations in regulatory elements of a gene. Examples of such mutations are described in Krawczak et al. (1992) *Hum. Genet,* 90:41-54; and Nakai et al. (1994) *Gene* 14:171-177. Other DTMR include disorders which have been attributed to a change in trans-acting factors. Examples of DTMRs which are associated with splicing include those described in Philips et al. (2000), *Cell. Mol. Life. Sci.,* 57:235-249), as well as, FTDP-17 (frontotemporal dementia with parkinsonism) and β-thalassemia.

Certain DTMRs associated with splicing include those which are generated by point mutations that either destroy splice-sites or generate new cryptic sites in the vicinity of normally used exons. Examples of such DTMRs include cystic fibrosis (Friedman et al. (1999) *J. Biol. Chem.* 274:36193-36199), muscular dystrophy (Wilton et al. (1999) *Neuromuscul. Disord.* 9:330-338), and eosinophilic diseases (Karras et al., (2000) *Mol. Pharamcol.* 58:380-387).

Other DTMRs include cancers which may change splicing patterns during cancer formation and progression. Example of such cancers include, but are not limited to leukemia, colon/rectal cancer, myeloid leukemia, breast cancer, gastric carcinomas, acute leukemia, multiple myeloma, myeloid cell leukemia, lung cancer, prostate cancer, etc. Addition DTMRs associated with splicing are discussed in Stoss et al., (2000), *Gene Ther. Mol. Biol.* 5:9-30).

Another example of a DTMR is a cancer in which treatment of the cancer cells with a tetracycline compound results in the modulation of RNA, where the modulation of RNA increases the susceptibility of the cell to a second agent, e.g., a chemotherapeutic agent. Such DTMRs can be treated using a combination of the tetracycline compound and a chemotherapeutic agent. Exemplary cancers include those in which the tetracycline compound modulates the form of BCL expressed by the cells.

Other DTMRs include disorders wherein particular ribozymes are present in aberrant quantities. Examples include breast cancer, hepatitis C virus (HCV), liver cirrhosis, and heptacellular carcinoma.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

The invention also pertains to pharmaceutical compositions comprising a therapeutically effective amount of a tetracycline compound (e.g., a tetracycline compound of the formula I, II, or otherwise described herein) and, optionally, a pharmaceutically acceptable carrier.

The language "pharmaceutically acceptable carrier" includes substances capable of being coadministered with the tetracycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is derivatized with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule. It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, II, or a compound otherwise described herein for the preparation of a medicament. The medicament may include a pharmaceutically acceptable carrier and the tetracycline compound is an effective amount, e.g., an effective amount to treat a tetracycline responsive state.

EXEMPLIFICATION OF THE INVENTION

Compounds of the invention may be made as described below and/or by using literature techniques known to those of ordinary skill in the art.

Example 1

Synthesis of 12-Dehydrodoxycycline

Triethylamine was added to a solution of doxycycline (1 g, 2.2 mmole) in 15 ml of methanol to bring the pH to about 9. Then, 426 mg of sodium borohydride (5 eq) was added to this mixture portionwise. The resulting reaction mixture was stirred at room temperature for several hours. The reaction was monitored by analytical HPLC and LCMS [MS: 445 (for starting material) and MS 447 (for product)]. The solvent was removed and the residue was diluted with water. The aqueous solution was then extracted with n-butanol (2×). The combined organic fractions were evaporated under reduced pressure to give the alcohol. This material was redissolved in 20 ml of trifluoroacetic acid and heated at 60 for several hours. The reaction was monitored by analytical HPLC and LCMS [MS: 447 for the alcohol and 429 for the dehydrated material). At the completion of the reaction, the TFA was evaporated and the residue was dissolved in a mixture of methanol/water (3:1). The solution was filtered and the desired material isolated via preparative HPLC. About 250 mg of light yellow solid was obtained (MS: 429). The chemical structure was further characterized by NMR.

1 mmol of 12-dehydrodoxycycline trifluoroacetate in 15 ml of DMF was reacted with 4 equivalent of amine and in the presence of 1 eq. of $InCl_3$. The reaction mixture was stirred at room temperature for several hours. The desired material was isolated via preparative HPLC.

12-Dehydrodoxycycline (4S,4aR,5S,5aR,6R,12aR)-4-Dimethylamino-3,5,10,12a-tetrahydroxy-6-methyl-1,11-dioxo-1,4,4a,5,5a,6,11,12a-octahydro-naphthacene-2-carboxylic acid amide (MS (M+H): 429.4)

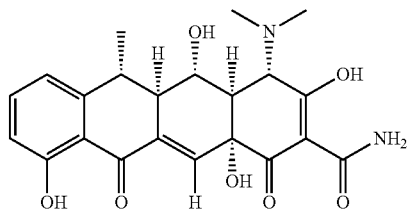 [SMILES: C[C@H]1c2cccc(O)c2C(=O)C2=C[C@]3(O)C(=O)C(C(N)=O)=C(O)[C@@H](N(C)C)[C@@H]3[C@@H](O)[C@@H]21]

The $^1H$, $^{13}C$ chemical shifts, and $^3J_{H\text{-}H}$ coupling constants of 12-dehydrodoxycycline are shown in Table 2 below.

TABLE 2

| Position | $^{13}C$ | $\delta^b$ | $\Delta^c$ | $^1H$ | $\delta^b$ | $\Delta^c$ | $^3J_{H\text{-}H}{}^{d,e}$ |
|---|---|---|---|---|---|---|---|
| 1 | 1 | 197.08 | 1.43 | — | — | — | — |
| 2 | 2 | 97.00 | 0.81 | — | — | — | — |
| 2a | 2a-CONH$_2$ | 174.57 | 0.42 | 2a-CONHa | N/O | — | N/O |
| — | — | — | — | 2a-CONHb | N/O | — | N/O |
| 3 | 3 | 187.96 | −0.25 | 3-OH | N/O | — | N/O |
| 4 | 4 | 67.75 | 0.60 | 4β | 4.43 | −0.02 | d, 0.9 |
| 4-NMe$_2$-a | 4-NMe$_2$-a | 43.81 | 0.30 | 4-NMe$_2$-a | 2.99 | −0.01 | s |
| 4-NMe$_2$-b | 4-NMe$_2$-b | 42.52 | 0.49 | 4-NMe$_2$-b | 2.98 | 0.05 | s |
| 4a | 4a | 44.33 | 1.19 | 4a | 2.69 | −0.14 | dd, 11.4, 1.2 |
| 5 | 5 | 71.56 | 1.51 | 5-OH | N/O | — | N/O |
| — | — | — | — | 5β | 3.61 | 0.04 | dd, 7.8, 7.8 |
| 5a | 5a | 50.61 | 2.73 | 5a | 2.63 | 0.04 | m |
| 6 | 6 | 40.25 | 0.09 | 6-Me | 1.60 | 0.05 | d, 6.6 |
| — | 6-Me | 17.68 | 1.40 | 6β | 2.81 | 0.06 | m |
| 6a | 6a | 149.68 | 0.44 | — | — | — | — |
| 7 | 7 | 117.22 | 0.52 | 7 | 6.96 | 0.01 | d, 7.8 |
| 8 | 8 | 138.33 | 0.45 | 8 | 7.48 | −0.01 | at, 7.8, 8.4 |
| 9 | 9 | 117.00 | −0.23 | 9 | 6.84 | 0.00 | d, 8.1 |
| 10 | 10 | 164.74 | 1.18 | 10-OH | N/O | — | N/O |
| 10a | 10a | 117.37 | 0.19 | — | — | — | — |
| 11 | 11 | 192.57 | −1.41 | — | — | — | — |
| 11a | 11a | 138.38 | 29.82 | — | — | — | — |
| 12 | 12 | 136.78 | −35.66 | 12 | 7.11 | — | d, 2.1 |
| 12a | 12a | 72.55 | −2.06 | 12a-OH | N/O | — | N/O |

[a]Chemical shifts in methanol-d$_4$. "N/O" means "Not Observed".
[b]Chemical shifts are in ppm, referenced to TMS as internal standard at 0 ppm.
[c]Differences are calculated by subtracting chemical shifts for Doxycycline from their corresponding chemical shifts in 12-dehydrodoxycycline.
[d]Coupling constants are in Hertz,
[e]"a", "b", "s", "d", "t", and "q" mean "apparent", "broad", "singlet", "doublet", "triplet", and "quartet" respectively.

Other Compounds Synthesized Using Similar
Methods Include

9-[(2,2-Dimethyl-propylamino)-methyl]-12-dehydro-doxycline (4S,4aR,5 S,5aR,6R,12aR)-4-Dimethylamino-9-[(2,2-dimethyl-propylamino)-methyl]-3,5,10,12a-tetrahydroxy-6-methyl-1,11-dioxo-1,4,4a,5,5a,6,11,12a-octahydro-naphthacene-2-carboxylic acid amide (MS (M+H): 528.6)

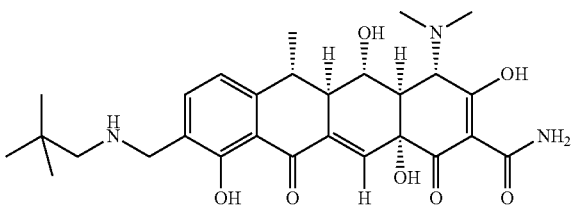 [SMILES: C[C@H]1c2ccc(CNCC(C)(C)C)c(O)c2C(=O)C2=C[C@]3(O)C(=O)C(C(N)=O)=C(O)[C@@H](N(C)C)[C@@H]3[C@@H](O)[C@@H]21]

9-Amino-12-dehydrodoxycline (4S,4aR,5S,5aR,6R,12aR)-9-Amino-4-dimethylamino-3,5,10,12a-tetrahydroxy-6-methyl-1,11-dioxo-1,4,4a,5,5a,6,11,12a-octahydro-naphthacene-2-carboxylic acid amide (MS (M+H): 444.4)

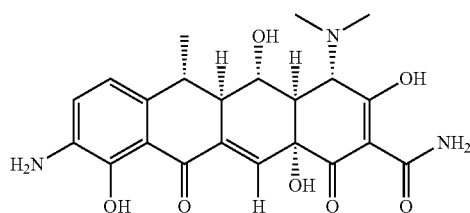 [SMILES: C[C@H]1c2ccc(N)c(O)c2C(=O)C2=C[C@]3(O)C(=O)C(C(N)=O)=C(O)[C@@H](N(C)C)[C@@H]3[C@@H](O)[C@@H]21]

9-bis-Dimethylamino-12-dehydrodoxycline (4S,4aR,5S,5aR,6R,12aR)-4,9-Bis-dimethylamino-3,5,10,12a-tetrahydroxy-6-methyl-1,11-dioxo-1,4,4a,5,5a,6,11,12a-octahydro-naphthacene-2-carboxylic acid amide (MS (M+H): 472.5)

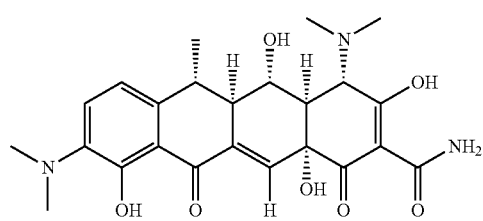 [SMILES: C[C@H]1c2ccc(N(C)C)c(O)c2C(=O)C2=C[C@]3(O)C(=O)C(C(N)=O)=C(O)[C@@H](N(C)C)[C@@H]3[C@@H](O)[C@@H]21]

12-Butylamino-12-dehydrodoxycycline 4S,4aR,5S,5aR,6R,12aS)-12-Butylamino-4-dimethylamino-3,5,10,12a-tetrahydroxy-6-methyl-1,11-dioxo-1,4,4a,5,5a,6,11,11a,12,12a-decahydro-naphthacene-2-carboxylic acid amide (MS: 502.5)

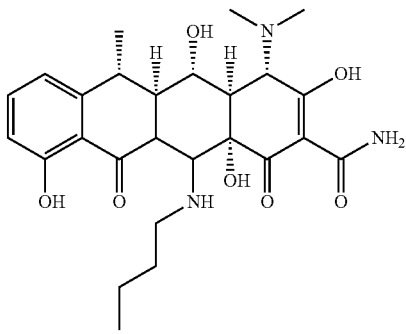 [SMILES: CCCCNC1C2C(=O)c3c(O)cccc3[C@H](C)[C@H]2[C@H](O)[C@H]2[C@H](N(C)C)C(O)=C(C(N)=O)C(=O)[C@@]12O]

12-Methylamino-12-dehydrodoxycycline (4S,4aR,5S,5aR,6R,12aS)-4-Dimethylamino-3,5,10,12a-tetrahydroxy-6-methyl-12-methylamino-1,11-dioxo-1,4,4a,5,5a,6,11,11a,12,12a-decahydro-naphthacene-2-carboxylic acid amide (MS: 460.2)

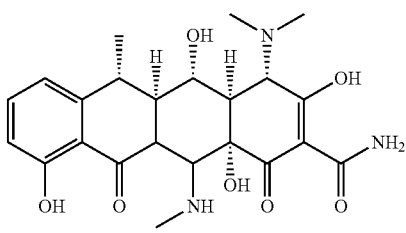 [SMILES: CNC1C2C(=O)c3c(O)cccc3[C@H](C)[C@H]2[C@H](O)[C@H]2[C@H](N(C)C)C(O)=C(C(N)=O)C(=O)[C@@]12O]

12-(2,2-dimethyl-propylamino)-12-dehydrodoxycycline (4S,4aR,5S,5aR,6R,12aS)-4-Dimethylamino-12-(2,2-dimethyl-propylamino)-3,5,10,12a-tetrahydroxy-6-methyl-1,11-dioxo-1,4,4a,5,5a,6,11,11a,12,12a-decahydro-naphthacene-2-carboxylic acid amide (MS: 516.6)

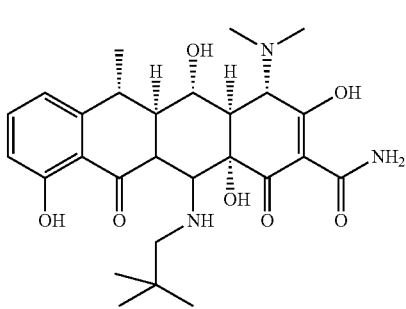 [SMILES: C[C@H]1c2cccc(O)c2C(=O)C2C(NCC(C)(C)C)[C@]3(O)C(=O)C(C(N)=O)=C(O)[C@@H](N(C)C)[C@@H]3[C@@H](O)[C@@H]21]

(4S,4aR,5S,5aR,6R,12aS)-4-Dimethylamino-3,5,10,12a-tetrahydroxy-6-methyl-1,11-dioxo-1,4,4a,5,5a,6,11,11a,12,12a-decahydro-naphthacene-2-carboxylic acid amide (MS: 431).

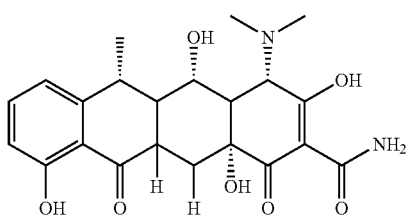 [SMILES: C[C@H]1c2cccc(O)c2C(=O)C2C[C@]3(O)C(=O)C(C(N)=O)=C(O)[C@@H](N(C)C)C3[C@@H](O)C21]

12-dehydrominocycline (4 S,4aS,5aR,12aR)-4,7-Bis-dimethylamino-3,10,12a-trihydroxy-1,11-dioxo-1,4,4a,5,5a,6,11,12a-octahydro-naphthacene-2-carboxylic acid amide (MS:M+H 442.5).

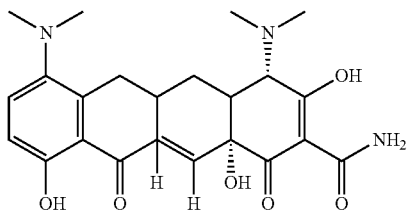

Example 2

In Vitro Minimum Inhibitory Concentration (MIC) Assay

The following assay was used to determine the efficacy of tetracycline compounds against common bacteria. 2 mg of each compound were dissolved in 100 µl of DMSO. The solution was then added to cation-adjusted Mueller Hinton broth (CAMHB), which resulted in a final compound concentration of 200 µg per ml. The tetracycline compound solutions were diluted to 50 µl, volumes, with a test compound concentration of 0.098 µg/ml. Optical density (OD) determinations were made from fresh log-phase broth cultures of the test strains. Dilutions were made to achieve a final cell density of $1 \times 10^6$ CFU/ml. At OD=1, cell densities for different genera were approximately:

| | |
|---|---|
| E. coli | $1 \times 10^9$ CFU/ml |
| S. aureus | $5 \times 10^8$ CFU/ml |
| Enterococcus sp. | $2.5 \times 10^9$ CFU/ml |

50 µl of the cell suspensions were added to each well of microtiter plates. The final cell density should be approximately $5 \times 10^5$ CFU/ml. These plates are incubated at 35° C. in an ambient air incubator for approximately 18 hours. The plates are read with a microplate reader and are visually inspected when necessary. The MIC was defined as the lowest concentration of the tetracycline compound that inhibits growth.

Compounds which were found to have low antibacterial activity include 12-dehydrodoxycycline, 9-bis-dimethylamino-12-dehydrodoxycline and 9-Amino-12-dehydrodoxycline.

Example 3

Demyelination-Related Disease Animal Model (DRDAM): In Vivo Experimental Autoimmune Encephalomyelitis (EAE) Murine Model In this example, a mouse model was used to determine the ability of the tetracycline compounds to treat demyelination related diseases. Other models which can be used are described in Brundula V. et al. *Brain* 2002 June; 125 (Pt 6): 1297-308 and Popovic N. et al. *Ann Neural.* 2002 February; 51(2):215-23.

To induce EAE, 6 week old C57BL/6 female mice were injected subcutaneously with 200 ug of myelin oligodendrocyte glycoprotein peptide (MOG 35-55) emulsified in 200 µL of complete Freund's adjuvant containing an additional 4 mg/mL of heat killed *M. tuberculosis*. Mice were additionally injected intravenously (tail vein) with 150 ng of lyophilized pertussis toxin resuspended in 150 µL PBS at time 0 and again 48 hours later. In this model, the mice developed progressive posterior to anterior advancing paralysis with symptoms first appearing at 10-12 days and progressing to severe paralysis by approximately 21 days. Severity of EAE was scored daily according to the following criteria: 0, healthy; 1, limp tail; 2, partial paralysis of one or two hind limbs; 3, complete paralysis of the hind limbs; 4, complete hind limb paralysis and forelimb paraparesis; 5, moribund. All test experiments included control groups of EAE induced mice treated with vehicle only or treated with minocycline, with 10 mice per group. Treatment began on day 10 (onset of disease) as IP injections with 50 mg/kg of minocycline, test tetracycline compound or vehicle alone each day until the end of the study. 12-Dehydrodoxycycline and 12-methylamino-12-dehydrodoxycycline were found to have activity similar to or better than minocycline.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A pharmaceutical composition comprising a compound selected from the group consisting of

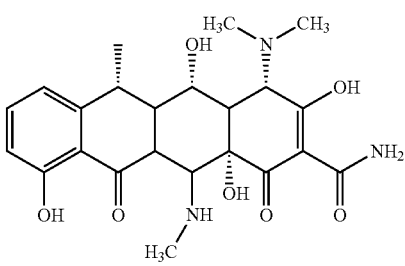

-continued

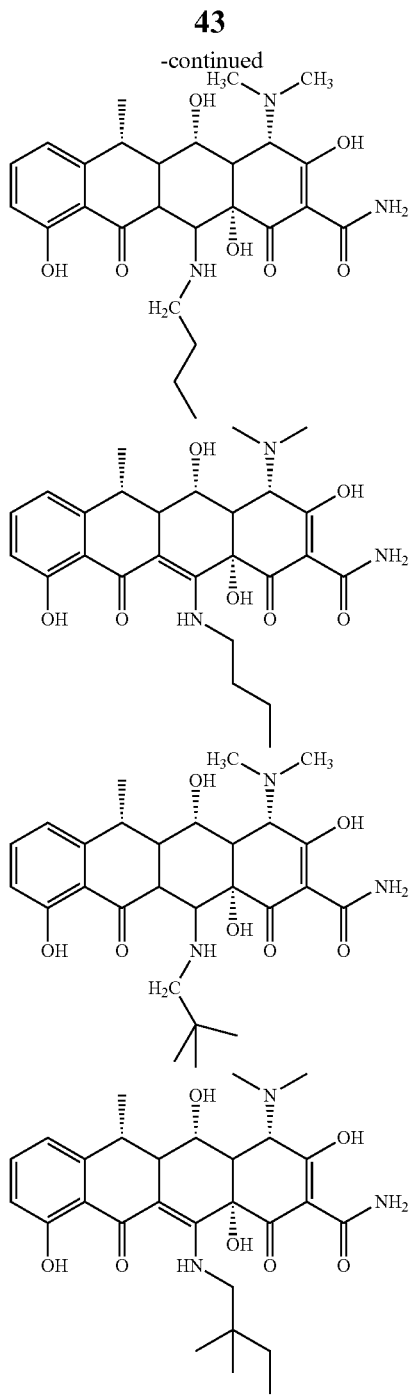

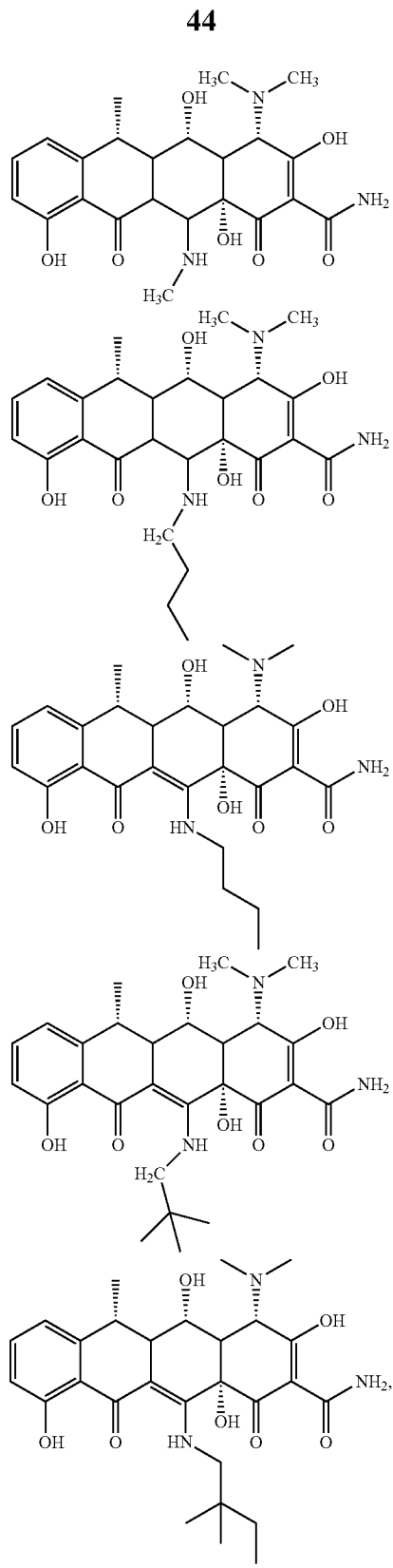

and a pharmaceutically acceptable carrier.

2. The pharmaceutical composition of claim 1, wherein said compound is present in an amount effective to ameliorate a disease selected from: bacterial infection, multiple sclerosis, central pontine myelinolysis, leukodystrophy, acute disseminated encephalomyelitis, progressive multifocal leukoencephalopathy, and subacute sclerosing panencephalitis.

3. A method for ameliorating a disease selected from: bacterial infection, multiple sclerosis, central pontine myelinolysis, leukodystrophy, acute disseminated encephalomyelitis, progressive multifocal leukoencephalopathy, and subacute sclerosing panencephalitis in a subject in need thereof, comprising administering to said subject an effective amount of a compound of selected from the group consisting of the following compounds:

such that said disease is ameliorated.

4. The method of claim 3, wherein said subject is a mammal.

5. The method of claim 3, wherein said subject is a human.

6. The method of claim 3, wherein said disease is bacterial infection.

7. The method of claim 3, wherein said disease is central pontine myelinolysis.

8. The method of claim 3, wherein said disease is leukodystrophy.

9. The method of claim 3, wherein said disease is acute disseminated encephalomyelitis.

10. The method of claim 3, wherein said disease is progressive multifocal leukoencephalopathy.

11. The method of claim 3, wherein said disease is subacute sclerosing panencephalitis.

12. The method of claim 3, wherein said disease is multiple sclerosis.

13. The method of claim 12, wherein said multiple sclerosis is relapsing or remitting multiple sclerosis, primary progressive multiple sclerosis, or secondary progressive multiple sclerosis.

* * * * *